United States Patent [19]

Don Michael

[11] Patent Number: 5,342,306
[45] Date of Patent: Aug. 30, 1994

[54] ADJUSTABLE CATHETER DEVICE

[76] Inventor: T. Anthony Don Michael, 4109 Sill Pl., Bakersfield, Calif. 93306

[21] Appl. No.: 67,119

[22] Filed: May 26, 1993

[51] Int. Cl.$^5$ ............................................. A61M 29/00
[52] U.S. Cl. ................................... 604/101; 604/53; 604/102; 606/194
[58] Field of Search ................ 604/53, 96, 101, 102, 604/103, 97, 98, 99; 606/191, 192, 194

[56] References Cited

U.S. PATENT DOCUMENTS

| | | | |
|---|---|---|---|
| 4,295,464 | 10/1981 | Shihata | 604/98 |
| 4,423,725 | 1/1984 | Baran et al. | |
| 4,573,966 | 3/1986 | Weikl et al. | 604/101 |
| 4,610,662 | 9/1986 | Weikl et al. | |
| 4,664,114 | 5/1987 | Ghodsian | 604/101 |
| 4,676,228 | 6/1987 | Krasner et al. | 604/101 |
| 4,911,163 | 3/1990 | Fina | 604/101 |
| 5,002,558 | 3/1991 | Klein et al. | 604/102 |
| 5,059,178 | 10/1991 | Ya | 604/96 |
| 5,090,960 | 3/1992 | Don Michael | 604/101 |
| 5,135,484 | 8/1992 | Wright | 604/101 |
| 5,163,905 | 11/1992 | Don Michael | 604/101 |

Primary Examiner—C. Fred Rosenbaum
Assistant Examiner—N. Kent Gring
Attorney, Agent, or Firm—Spensley Horn Jubas & Lubitz

[57] ABSTRACT

A method and apparatus for performing a medical treatment at a selected location of a physiologic passage by: introducing the apparatus into the passage so that a first location on the catheter is opposite the selected location of the passage; establishing a selected spacing between first and second balloons carried by the apparatus and inflating the first and second balloons to establish a treatment region which is bounded by the balloons, the catheter and the passage; periodically introducing a treatment chemical into the treatment region and withdrawing fluid from the treatment region via means for permitting flow and a first lumen of the apparatus; and during the course of the step of periodically introducing, varying the spacing between the first and second balloons.

5 Claims, 1 Drawing Sheet

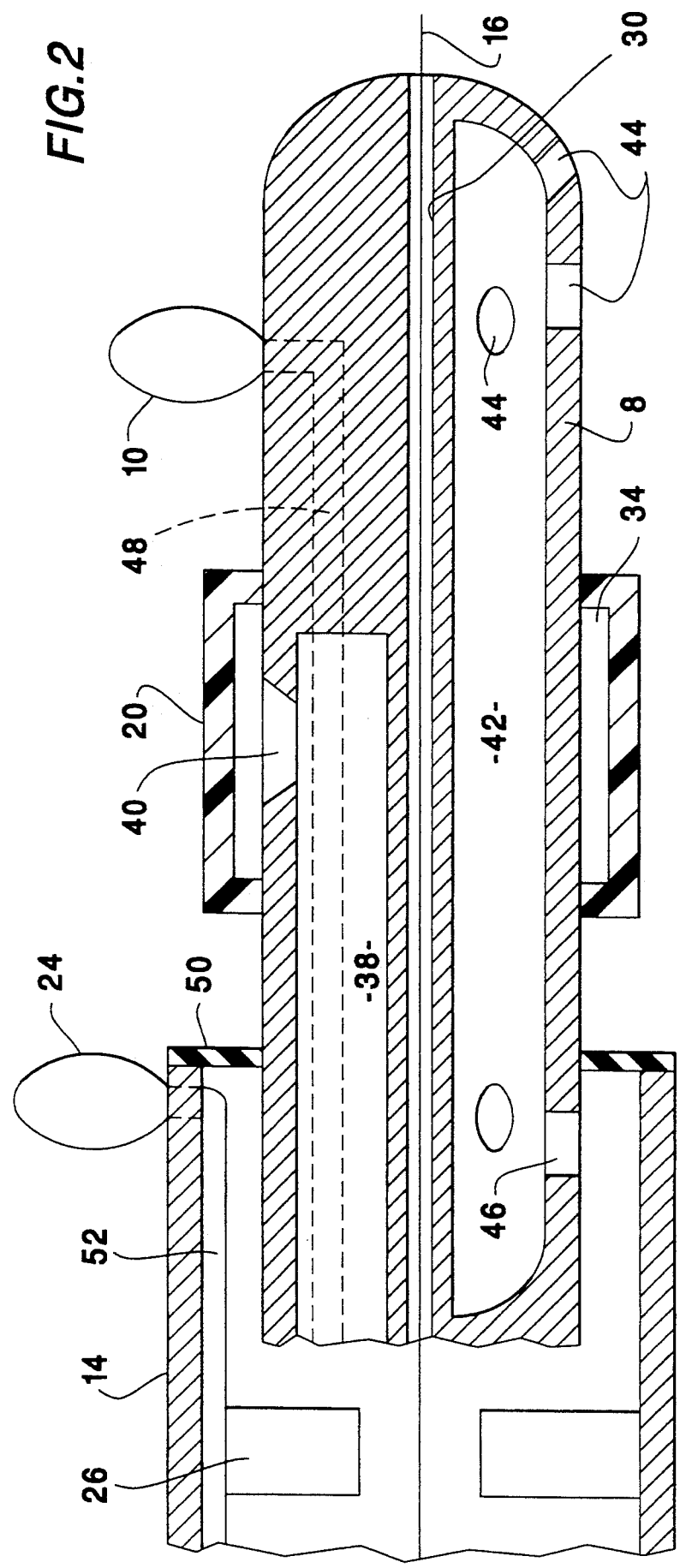
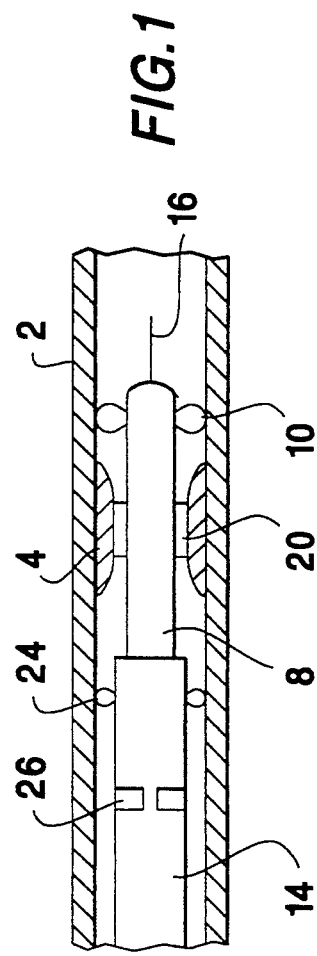

ADJUSTABLE CATHETER DEVICE

CROSS-REFERENCE TO RELATED APPLICATIONS

This application relates to subject matter disclosed in Applicant's copending U.S. application Ser. Nos. 868,961, filed Apr. 16, 1992; 808,924U.S. Pat. No. 5,222,941, filed Dec. 18, 1991; and 919,238, filed Jul. 27, 1992, the contents of which are incorporated herein by reference, and U.S. Pat. No. 5,090,960, issued Feb. 25, 1992.

BACKGROUND OF THE INVENTION

The present invention relates to apparatus and methods for performing treatments in physiologic passages, and particularly for performing treatments involving the use of chemical, biological, etc. agents in a selected portion of a blood vessel.

As disclosed in my copending applications and patent, a variety of abnormal conditions associated with physiologic passages can be treated by bringing a selected chemical, biologic, or genetic agent into contact with the wall of the passage or with obstructing material which has developed on the passage wall. For this purpose, a region of the passage may be isolated, while the fluid normally carried by the passage is permitted to continue to flow past the isolated region. Such apparatus permits a variety of treatments to be performed in an effective manner.

SUMMARY OF THE INVENTION

It is an object of the present invention to enhance the control of such procedures.

A more specific object of the invention is to permit ready adjustment of the length of the isolated region.

The above and other objects are achieved, according to the present invention, by apparatus for performing medical treatments in a physiologic passage, comprising: a catheter insertable into the physiologic passage, the catheter having a distal end, a proximal end, a first lumen extending from the proximal end and means for permitting bidirectional flow of a fluid between the first lumen and a region surrounding the catheter at a first location spaced from the distal end; a first balloon carried by, and extending radically outwardly from, the catheter at a second location between the distal end and the first location, the first balloon being inflatable for inhibiting fluid flow through the physiologic passage and around the catheter; and control means including a second balloon surrounding the catheter in a region between the proximal end and the first location, the control means being movable for varying the spacing between the first and second balloons and being operative, upon inflation of the second balloon, to inhibit fluid flow through the physiologic passage and around the catheter.

Objects according to the invention are further achieved by a method of performing a medical treatment at a selected location of a physiologic passage by use of the apparatus described above, comprising: introducing the apparatus into the passage so that the first location on the catheter is opposite the selected location of the passage; establishing a selected spacing between the first and second balloons and inflating the first and second balloons to establish a treatment region which is bounded by the balloons, the catheter and the passage; periodically introducing a treatment chemical into the treatment region and withdrawing fluid from the treatment region via the means for permitting flow and the first lumen; and during the course of the step of periodically introducing, varying the spacing between the first and second balloons.

With the apparatus according to the present invention, the effective length of the treatment region can be adjusted at will. Such adjustment can serve, inter alia, the following purposes:

If it should be determined, based on the analysis of a sample of fluid taken from the treatment region, that the concentration of treatment agent in the region is excessively high, the length of the treatment region can be abruptly increased to draw a portion of the fluid which is normally present in the body passages into the treatment region from locations adjacent the treatment region; and If the condition encountered in the physiologic passage is such that a treatment should be performed exclusively on a limited portion of the effected region, the balloons can be positioned relative to one another to achieve this result. Such a procedure might be beneficial, for example, in the case of an obstruction having several portions with distinctly different characteristics, each of which is treated most effectively in a specific manner.

BRIEF DESCRIPTION OF THE DRAWING

FIG. 1 is a side elevational view illustrating the basic components of apparatus according to the invention, in position in a physiologic passage.

FIG. 2 is a cross-sectional view showing the apparatus of FIG. 1 in greater detail.

DESCRIPTION OF THE PREFERRED EMBODIMENTS

FIG. 1 illustrates the distal end of a preferred embodiment of apparatus according to the invention inserted into a physiologic passage 2, for example a blood vessel in which an obstruction 4 has developed. The apparatus is composed of a catheter 8, a balloon 10 carried by catheter 8, and a hollow tubular member 14 surrounding catheter 8. FIG. 1 further shows a guide wire 16 via which the apparatus would be advanced to the desired location in passage 2 in a conventional manner.

Catheter 8 carries a member 20 which permits fluid to flow between a region surrounding catheter 8 and a lumen 38 in FIG. 2 within catheter 1.

Tubular member 14 carries a second balloon 24 and is provided with openings 26 the purpose of which will be described below.

When balloons 10 and 24 are inflated, as shown in FIG. 1, they inhibit fluid flow through passage 2, around catheter 8 and tubular member 14, respectively, and thus create a partially or completely isolated treatment region for performing a variety of treatments, as described in the above-cited copending U.S. applications and patent.

Balloons 10 and 24 are low pressure, high compliance balloons, which means that they are capable of expanding, and conforming to their surroundings, in response to a relatively low inflation pressure. Therefore, when balloons 10 and 24 are inflated while in passage 2, they will expand circumferentially as well as radially to substantially completely fill the annular region between the wall of passage 2 and catheter 8 or tubular member 14, respectively, without stretching the wall of passage 2.

Thus, in their inflated state, balloons 10 and 24 can partially or completely block fluid flow through those annular regions.

FIG. 2 shows the apparatus of FIG. 1 in greater detail and with balloons 10 and 24 deflated. Catheter 8 is provided with a central lumen 30 which extends from the proximal end (not shown) to the distal end of catheter 8 for passage of guide wire 16.

Member 20 encloses a space 34 and catheter 8 is provided with a second lumen 38 which communicates with space 34 via an opening 40 which extends to the outer surface of catheter 8. Member 20 may be made of a material which inherently has a high degree of porosity or may be provided with holes to permit passage of fluid between lumen 38 and the treatment region surrounding member 20. In particular, a treatment chemical may be delivered to the treatment region or a fluid sample may be withdrawn from the treatment region in connection with procedures as described in the above-cited copending applications. Such treatments can include periodically withdrawing a fluid sample from the treatment region and analyzing the withdrawn sample to determine the concentration of treatment chemical therein.

Catheter 8 further includes a bypass flow path constituted by a closed lumen 42, openings 44 which extend to the surface of catheter 8 in the vicinity of its distal end, and openings 46 which extend to the surface of catheter 8 at a location which is between the proximal end of catheter 8 and member 20. A fluid, such as blood, which normally flows through passage 2 can bypass the region enclosed by balloons 10 and 24 via this bypass flow path. Catheter 8 also includes a balloon inflation lumen 48 which is illustrated by broken lines in FIG. 2, since, in the plane of that Figure, lumen 48 is hidden.

Tubular member 14 carries an annular seal member 50 which bears against the outer surface of catheter 8 to seal the annular space between catheter 8 and tubular member 14. Tubular member 14 also carries a thin tube, or lumen, 52 for supplying inflation fluid to balloon 24. Finally, tube 24 is provided with openings 26 which provide a fluid flow path between openings 46 and a region of passage 2 which is outside tubular member 14 and between balloon 24 and the proximal end of the apparatus. To maintain flow through the bypass flow path, movement of tubular member relative to catheter 8 is limited to a range in which seal member 50 remains between at least one of openings 46 and member 20. Of course, the distance between openings 46 and member 20 can be given any desired value.

Because the spacing between balloons 10 and 24 can be varied, while maintaining an isolated region between the balloons, it is possible, according to the invention, to abruptly increase or reduce the volume of the treatment region, or to set the length of the treatment region to a given value so that a particular treatment can be confined to a defined region. As a result, the modified apparatus according to the present invention opens new possibilities for the types of treatment in which a treatment agent, such as a chemical agent, a biological agent, or a genetic agent, is brought into contact with a region of a body passage, and is maintained in that region, with a given concentration, for a period of time sufficient to produce a desired result. In the use of apparatus according to the invention, at the end of a treatment for removing an obstruction 4, balloon 24 may be deflated and the apparatus 8, 24 can be withdrawn while balloon 10 remains inflated and suction continues to be applied at the treatment region, e.g. via lumen 38, opening 40 and region 34. Thus, balloon 10 can loosen material which may continue to adhere to the wall of passage 2 and the loosened material can then be removed by the suction.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

I claim:

1. Apparatus for performing medical treatments in a physiologic passage, comprising:

a catheter insertable into the physiologic passage, said catheter having a distal end, a proximal end, a first lumen extending from said proximal end and means for permitting bidirectional flow of a fluid between said first lumen and a region surrounding said catheter at a first location spaced from said distal end;

a first balloon carried by, and extending radially outwardly from, said catheter at a second location between said distal end and said first location, said first balloon being inflatable for inhibiting fluid flow through the physiologic passage and around said catheter; and control means including a second balloon surrounding said catheter in a region between said proximal end and said first location, said control means being movable for varying the spacing between said first and second balloons and being operative, upon inflation of said second balloon, to inhibit fluid flow through the physiologic pressure and around said catheter, wherein said catheter is provided with means defining a bypass flow passage extending along a portion of the length of said catheter and communicating with regions surrounding said catheter at third and fourth locations along the length of said catheter such that when said catheter is in a passage, said third and fourth locations are positioned upstream and downstream, respectively, of the region enclosed by said balloons, and said control means comprise a tubular member surrounding said catheter and carrying said second balloon, said tubular member having an opening defining a passage in fluid flow communication with said bypass flow passage.

2. Apparatus as defined in claim 1 wherein said control means comprise a tubular member surrounding said catheter and carrying said second balloon, and seal means forming a seal which prevents fluid flow between said catheter and said second balloon.

3. Apparatus as defined in claim 2 wherein said seal means comprise an annular seal member carried by said tubular member and forming a seal with said catheter.

4. A method of performing a medical treatment at a selected location of a physiologic passage by use of apparatus composed of a catheter having a distal end, a proximal end, a first lumen extending from the proximal end and means for permitting bidirectional flow of a fluid between the first lumen and a region surrounding the catheter at a first location spaced from the distal end, a first balloon carried by, and extending radially outwardly from, the catheter at a second location between the distal end and the first location, the first balloon being inflatable for inhibiting fluid flow through the physiologic passage and around the catheter, and control means including a second balloon surrounding the catheter in a region between the proximal end and the first location, the control means being movable for varying the spacing between the first and second balloons and being operative, upon inflation of the second balloon, to inhibit fluid flow through the physiologic passage and around the catheter, said method comprising:

introducing the catheter into the passage so that the first location on the catheter is opposite the selected location of the passage;

establishing a selected spacing between the first and second balloons and inflating the first and second balloons to establish a treatment region which is bounded by the balloons, the catheter and the passage;

periodically introducing a treatment chemical into the treatment region and withdrawing fluid from the treatment region via the means for permitting flow and the first lumen; and during the course of the step of periodically introducing, varying the spacing between the first and second balloons.

5. A method as defined in claim 4 wherein said step of varying the spacing comprises rapidly increasing the spacing between the balloons.

* * * * *